United States Patent [19]

Clynes

[11] 3,995,492
[45] Dec. 7, 1976

[54] SOUND-PRODUCING ISOMETRIC EXERCISER

[76] Inventor: Manfred E. Clynes, 8571 Villa LaJolla Drive, LaJolla, Calif. 92037

[22] Filed: Aug. 11, 1975

[21] Appl. No.: 603,781

[52] U.S. Cl. .............................. 73/379; 340/384 E
[51] Int. Cl.² .......................................... G01L 5/02
[58] Field of Search ........ 73/379, 380, 381, 141 A; 340/384 E

[56] References Cited
UNITED STATES PATENTS

| | | | |
|---|---|---|---|
| 1,623,869 | 4/1927 | Giraldi | 73/380 |
| 3,349,621 | 10/1967 | Mullen | 73/380 |
| 3,563,097 | 2/1971 | Roggenstein et al. | 73/141 |
| 3,672,219 | 6/1972 | Patten | 73/379 |
| 3,689,832 | 9/1972 | Leto | 324/65 R |
| 3,742,491 | 6/1973 | Lawson | 340/384 |
| 3,754,438 | 8/1973 | Matson | 73/141 |
| 3,864,966 | 2/1975 | Seitz | 73/141 |
| 3,872,476 | 3/1975 | Hoerz et al. | 340/384 |

OTHER PUBLICATIONS

Wilkie, The Relation Between Force & Velocity in Human Muscle, in Journal or Physiology, vol. 110–111, 1949–1950, p. 270.

Primary Examiner—Herbert Goldstein

[57] ABSTRACT

An isometric exerciser formed by a pair of spaced bodies joined together by a link associated with a transducer and ensheathed in a cover to define a structure having a generally oblong configuration. By grasping the ends of the exerciser in his hands, a user is able to exert a compressive or tension force on the transducer. The transducer converts this force into a corresponding electrical value that is applied to a pulse generator coupled to a loudspeaker housed within the structure, thereby producing a train of audible pulses whose repetition rate, tone and amplitude depend on the applied force. Thus the user receives a continuous audible feedback, permitting him to adjust the applied force to a desired level. By means of a counter responsive to the output of the pulse generator, one is able to score the user's performance.

14 Claims, 5 Drawing Figures

SOUND-PRODUCING ISOMETRIC EXERCISER

BACKGROUND OF INVENTION

This invention relates generally to the development of muscular skills, and more particularly to a hand-held isometric exerciser that is usable to execute various arm and other movements, the exerciser generating audible signals which reflect the degree of pressure or tension exerted by the user.

Exercisers based on isometric principles require the user to strain his muscles against an immovable object for a short time period so that the user is able to experience a large muscle strain at a constant muscle length. As a consequence, the fiber links of the muscles remain constant or in isometric contraction, thereby improving muscular development and tone.

Despite the gains in muscle strength and development obtainable through isometric exercising, existing devices for this purpose fail to give satisfactory results, for the benefit of exercising tends to diminish rather than increase with continued use.

The coordinated brain control of the muscles are such as to defeat the function of ordinary isometric exercisers. The reason for this is that the user learns and his conscious or unconscious mental process adapts to the fact that however much effort the muscles exert in either pulling or pushing against an immovable object, the object will not move. Hence, when continuing to perform isometric exercises with conventional devices, a point is quickly reached where brain control recognizes the futility of having the muscles strain to move an immovable object, and it causes what amounts to an involuntary release of muscle strain.

Another drawback characteristic of existing types of isometric exercisers is the restriction it imposes on body movement. The typical exerciser precludes or limits arm and leg movement, as a result of which continued use of the exerciser gives rise to tedium. Though the user is aware of the physical benefits to be gained by isometric exercising, boredom discourages him from persisting in this form of exercise. Moreover, conventional exercising serves only to improve a limited set of muscles and neglect many others important to proper muscular development.

Another factor which militates against the use of conventional isometric exercisers is the absence of diversion or sports activity. In sports, one develops skills and improves physical fitness in competition with other players. But with isometric exercisers of the known type, the user merely exerts muscle power without regard to the power exercised by another user and therefore without any incentive to improve his power and skill against that of a competitor.

The difficulties experienced with isometric exercisers are encountered with most other non-competitive exercising devices, for such exercising activity can be psychologically depressive and unrewarding. Thus while one who rows a boat has the satisfaction of movement and of reaching a destination, the user of a rowing machine goes nowhere and finds it difficult, therefore, to sustain this monotonous exercise.

SUMMARY OF THE INVENTION

In view of the foregoing, the main object of this invention is to provide an isometric exerciser in which the effort exerted by the user against a seemingly-immovable object is reflected by an audible signal whose nature varies as a function of the applied force.

Because of the correlation between the nature of the audible signal and the applied pulling or pushing force, the exerciser affords continuous feedback. Thus the user is positively reinforced or rewarded rather than frustrated, and while the application of force produces no perceptible movement of the object against which it is exerted, its translation into an audible signal causes the user's brain control to recognize the performance of the muscles. As a result, continued use of the exerciser gives rise to increasing rather than diminishing benefits.

Also an object of the invention is to provide a highly compact exerciser which is holdable between the hands whereby as the user exerts pressure or tension thereon, he can at the same time execute a large variety of free arm and other movements. Because of its maneuverability, the benefits derived from the exerciser encompass the kinematic as well as the isometric field.

Yet another object of this invention is to provide an exerciser which is usable as a sporting device to play competitive games in the course of which the players gain agility and skill as well as improving their muscular development and tone.

Briefly stated, these objects are attained in an exerciser formed by a pair of spaced bodies which are joined together by a link associated with a transducer, these elements being ensheathed by a yieldable cover to define a structure having an oblong configuration that is holdable between the hands of a user.

By grasping the ends of the exerciser, a user is able to exert a compressive or tension force on the link, depending on whether the user tries to pull the bodies apart or to push them together. The transducer associated with the link converts the physical force to which it is subjected into a corresponding electrical value. This value is applied to a pulse generator coupled to a loudspeaker housed within the structure, thereby producing a train of audible pulses whose repetition rate, tone and amplitude depend on the strength of the applied force. Thus the user receives a continuous audible feedback which permits him to adjust the force being applied to the exerciser to a desired level. The sound also gives the user a sense of satisfaction when it acquires a character indicative of the optimum force for a given exercise.

By conveying the generated pulses to a scoring system that includes a counter, one obtains an achievement score, making it possible for the user to pit his skill and strength against a competitor. Because the exerciser is compact and easily held, one is able to swing the exerciser through circular and other patterns of arm movement while the hands continue to apply a steady force thereto. As these maneuvers are executed, the user, by means of the audible signal, is able to maintain the desired degree of pressure.

OUTLINE OF THE DRAWINGS

For a better understanding of the invention as well as other objects and further features thereof, reference is made to the following detailed description to be read in conjunction with the accompanying drawings wherein.

DESCRIPTION OF INVENTION

Figure 1:
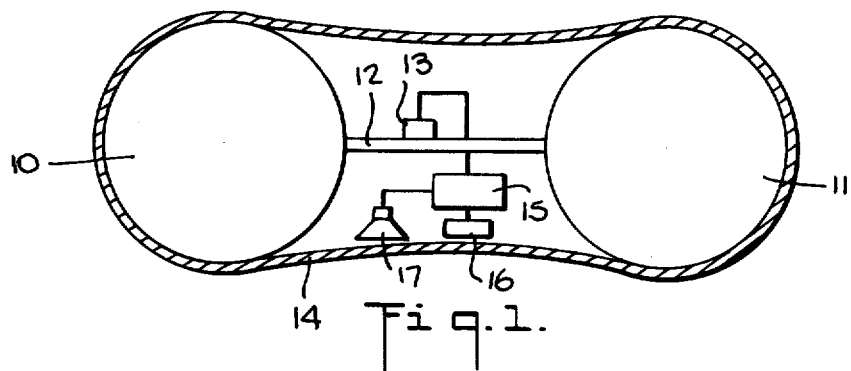
FIG. 1 is a section taken through a preferred embodiment of an exerciser in accordance with the invention.

Referring now to the drawing and more particularly to FIG. 1, there is shown a preferred embodiment of an exerciser in accordance with the invention, the exerciser being constituted by a pair of ball-shaped bodies 10 and 11 in spaced relation, the bodies being joined together by a link 12. Associated with link 12 is a pressure-sensitive transducer 13.

These elements are ensheathed in a removable mantle or cover 14 to define a structure having a generally oblong configuration. In practice, the total length of the structure is preferably less than 12 inches, so that the ends may easily be grasped by the hands of a user while the exerciser is manipulated in various ways to be later described. In practice, bodies 10 and 11 at the ends of the structure may be contoured or ridged to provide more grippable surfaces resisting slippage.

Though the bodies and link therebetween are of rigid material, preferably of molded plastic, the cover 13 is not a hard unyielding surface but has a natural feel which is obtained, for example, by a fabric having a wool, plush or fur pile, by padded leatherette or by a stretch fabric laminated to flexible foam plastic material.

The cover is provided with a zippered fly so that one has access to the interior structure for replacing batteries or repair. The texture of the cover surface is preferably such as to provide a pleasurable, or sensuous tactile experience, and it should be washable and replaceable so that different cover textures and colors may be provided to satisfy individual tastes.

Transducer 12 may be any device capable of converting the applied compression or tension force into a corresponding electrical value. For this purpose, use may be made of a piezoelectric pressure-responsive element, a strain gauge, a carbon powder device, a solid-state pressure transducer or other suitable means.

Figure 2:
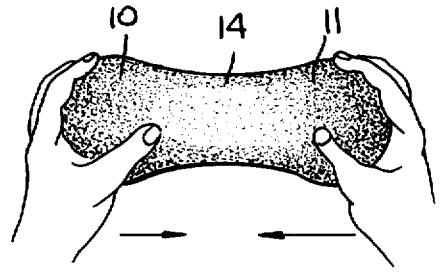
FIG. 2 shows the exerciser held by the user in the compression mode.
Figure 3:
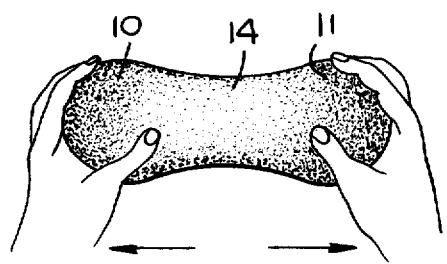
FIG. 3 shows the exerciser held by the user in the tension mode.

When the user pushes against the pads of the exerciser, as shown in FIG. 2, an electrical value is generated by the transducer which reflects the applied compressive force. And when the user pulls the ends of the exerciser apart, as shown in FIG. 3, tension is then applied to the transducer, the electrical value produced thereby being an analog function of the applied tension. But since an applied tension will have the reverse effect on the transducer, a tension force equal to a pressure force will produce a transducer output of the same magnitude but of opposite sign.

In order, therefore, to provide an audible output which is independent of the direction of the applied force, a switch is provided that is responsive to the direction of the force applied to the structure to reverse the output of the transducer when it is subjected to tension. Thus when an applied tension force is equal in magnitude to an applied compression force, the output will be the same both in magnitude and sign.

Alternatively, to obviate the need for a switch, the transducer may be in the form of a pair of sensitive elements providing equal outputs of opposite sign, so that when pressure is applied, one element produces a positivegoing voltage while the other produces a negative-going voltage, whereas when tension is applied, the reverse output voltages are obtained. By associating the two elements of the transducer with an appropriate rectifying demodulator, one can exclude the negative-going voltages and obtain from the combined elements a positive-going voltage both in compression and tension.

Also included is a battery-operated pulse-generating system, preferably in integrated circuit form and generally designated by numeral 15, which converts the transducer output value to an audible signal whose nature is indicative of the applied force. This system, as well as a battery 16 therefor, is housed in a suitable casing contained in the structure, the casing including a hatch to provide access thereto to replace the battery. The output of the system is applied to a miniature loudspeaker 17 mounted on the wall of the casing so that it can be easily heard by the user.

Because of the compact structure, it becomes possible to apply a steady, controlled pressure or tension to the ends thereof, while concurrently executing various free movements, so that body control as well as muscle development may be improved in the course of practice. The exerciser lends itself to a great variety of movements comparable to that executed by a figure skater on ice. Thus one can negotiate figure eights and free forms as well as elliptic and other geometric forms including straight lines at various angles in space and in all possible planes.

The person using the exerciser has great freedom to execute movements that will involve many different groups of muscles in a single movement pattern. For example, maintaining constant pressure while executing a 2½ foot diameter circle at a 45° inclination to the body, with one circle formed every two seconds, brings into play various muscle groups involving the agonist and antagonist groups of forearm, upper-arm, shoulder and torso, these groups are involved with different phases of the circular motion.

To execute a smooth movement while maintaining constant pressure entails considerable alertness and muscular control. Similarly, a figure eight or a circle executed horizontally with arms held above the head so that the exerciser is above the head, brings into operation various groups of muscles during the execution of this figure.

In using the exerciser, pressure and tension may be alternated for the same movement pattern, thereby stimulating both sets of muscle groups and preventing fatigue of either. Thus typically one might execute five circles in a six second period in a given plane in compression, followed by the same number of circles in the same plane in tension. The same two sequences are then repeated in the opposite sense of rotation. The movement pattern might also be ABB'A', where A and A' refer to pressure in opposite direction of rotation and B and B' are tension in opposite direction of rotation, respectively.

The ability to execute these choreographic patterns and sequences lends a ceremonial touch thereto that creates a feeling of symmetry and balance that one might associate with such practices as tea ceremonies or such disciplines as Tai Chi. A sequence of movements allows the user creative freedom while at the same time providing him with healthful exercise, development of skill and control. It also provides an exercise in orientation in space, developing the kinesthetic sense, invaluable for the control and development of dancers.

Figure 4:
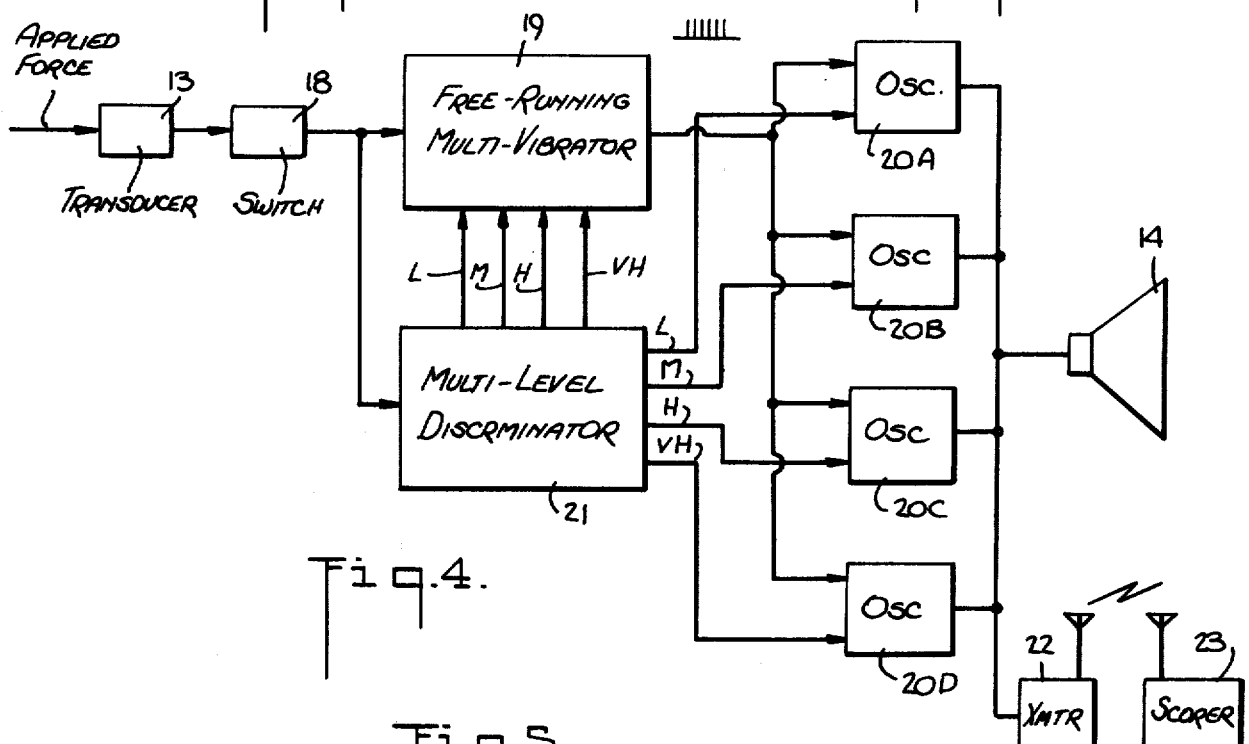
FIG. 4 is a block diagram illustrating the circuit of the audible signal generating system.

Referring now to FIG. 4, a preferred embodiment of the audible signal-generating system is shown in block diagram. It will be seen that the output of transducer 13 is applied through a reversing switch 18 to the input of a free-running multivibrator 19, the switch being mechanically-responsive to a pulling or pushing force so as to apply to the multivibrator an electrical value that is always of the same sign. The free running multivibrator produces pulses at a repetition rate that depends on the magnitude of the applied transducer input so that as the input rises, the repetition rate increases accordingly. As pointed out previously, by using a two-element transducer having a positive-going output regardless of the direction of the applied force, one may dispense with switch 18.

The output pulses of multivibrator 19 is applied to a set of four normally-quiescent oscillators 20A, 20B, 20C, and 20D, each having a different frequency and amplitude within the audio range, the pulses triggering whichever oscillator is rendered operative by a multi-level discriminator 21. Thus, by way of example, oscillator 20A generates a 200 Hz tone at one amplitude level, oscillator 20B generates a 300 Hz tone at a somewhat higher amplitude level, oscillator 20C generates a 500 Hz tone at a still higher level and oscillator 20D generates an 800 Hz tone at the highest amplitude level. It is to be understood that in practice the exerciser may include a fewer number of tone or pitch changes, or a greater number thereof.

The oscillators in the set are assigned different force bands. If, therefore, the range of forces applicable to the exerciser is divided into four bands: low (L), medium (M), high (H), and very high (VH), then by means of multi-level discriminator 21, which has a different threshold for each of the bands, the discriminator 21 acts through suitable gates, to render the appropriate oscillator operative.

Figure 5:
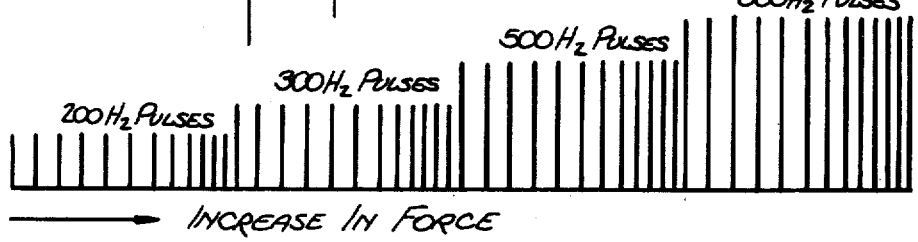
FIG. 5 is a wave form illustrating the output of the signal generating system.

The operative oscillator is then triggered on by the multivibrator output so that when the low-force band oscillator 20A is operative, it produces tone pulses or beeps of 200 Hz at a repetition rate which depends on the magnitude of the applied force. As the force rises to the level of the next band, oscillator 20B is rendered operative to produce 300 Hz beeps, and so on, as illustrated in FIG. 5.

In this way the player, by the tone he hears, knows whether the force he is applying is of a strength falling into the low, medium, high or very high band, and by the repetition rate of the pulses he is advised whether the force he is applying within a given band is steady, increasing or diminishing.

Free-running multi-vibrator 19 is under the bias control of multi-level discriminator 21 so that the repetition rate of its output pulses varies from the same minimum to the same maximum value in each of the force bands, L, M, H and VH. For example, a useful repetition rate range for this purpose is 1 to 15 pulses per second (pps), the 1 pps rate representing the minimum force exerted by the user at any force band, whereas the 15 pps rate represents the maximum force.

A user is responsive to the rhythmic beeps produced in this 1 to 15 pps range, for if the objective in a given exercise is to apply and maintain a force of 3 beeps per second in the middle force band H, by the distinct tonal pitch of the beep, the user knows whether he is in the proper force band, and by the distinct rhythm of the beeps he also knows whether he is applying the required force in said band. Thus discriminator 21 functions to apply a bias to multivibrator 19 appropriate to the operative force band, so that in response to the analog input representing the applied force, the multivibrator output repetition rate assumes a sawtooth pattern.

In practice, instead of having each beep tone at a fixed predetermined amplitude, the oscillators may be made responsive to the pulse repetition rate so that the greater the rate, the louder the tone. In this way, as the user increases the force applied to the exerciser, the tone of the beeps steps up in pitch, the loudness of the tone generated by the operative oscillator increases, and the repetition rate also increases.

For purposes of scoring in competitive play, the output of the oscillators may be transmitted by a miniature radio transmitter 22 incorporated within the structure to an external receiving station 23 having a digital counter adapted to count the received signal. Counting the signals within a fixed time interval, which depends on whatever period is chosen for a specified movement pattern measures the time interval of force. Alternatively, such transmission may be carried out by a wire connection or by means of a microphone which picks up the audible beeps.

The counting system is arranged to count the number of tone cycles received within a predetermined period, not the number of beeps. If, for example, the time duration of each beep is 1/10th of a second and the tone frequency in the low force band L is say 100 Hz, then 10 cycles of tone will be contained in each beep. And if the counting system is set to time a 10-second interval and the beep rate is 2 per second, then in the 10-second interval, the total count will be 200.

In order to have the count increase proportionally as one steps from one force band to the next higher band, even though the pulse repetition rate range is the same in all bands, the duration of the pulses produced in the higher band must be increased, taking into account that in the higher band the tone has a higher pitch and therefore provides more cycles per second. Thus the biasing system for the multivibrator is made such that while the pulse repetition rate range for each force band is the same, the pulse duration is stepped up as one goes from one force band to the next.

The timer associated with the counter must indicate to the user, by way of lights or other signals, the beginning and end of the timing interval. Where the exercise being performed involves a series of steps or manoeuvres, the timer can be programmed to provide signals at the beginning and end of each manoeuvre, with an appropriate dead space between manoeuvres to allow the user to shift position from one manoeuvre to the next, so that counting only takes place during the manoeuvre periods to provide a fair score.

The object of such scoring is not to determine which performer or player has attained the highest score (although it can also be so used) but to determine who has come closest to the ideal score, in the fashion of a bullseye. Thus for each type of movement repeated a given number of times, there is an ideal score, and for the total sequence of movements there is an ideal aggregate score. The fact that the exerciser can be used for sport activity is but one of its many attractive aspects. The production of rhythmic sounds which accompany the user's exertions is, per se, a source of pleasure and amusement.

While there has been shown and described a preferred embodiment of a sound-producing isometric exerciser in accordance with the invention, it will be appreciated that many changes and modifications may be made therein without, however, departing from the essential spirit thereof. Thus, while the structure has been described as composed of a pair of bodies, joined together by a link, it will be appreciated that these elements can be integrated into a unitary structure rather than composed of distinct components. Also the timbre of the tones may be made different in compression (i.e., — hollow tones) from tension (nasal tones).

Furthermore the exerciser may incorporate setting means to calibrate the system to produce a given number of beeps at a standard pressure. A particular advantage of the device is that it permits exercise or play within a confined area, while still involving muscular effort, skill, scorability and competitiveness. It may therefore by used by invalids in hospitals as well as in schools and old-age homes.

In practice, the ends of the exerciser may be provided with handles in strap or other suitable form to facilitate the engagement therewith, by the feet of the user or by one foot and one hand rather than by both hands. The free moving exerciser is particularly useful in rehabilitation centers. Because of its scorability, it lends itself to graduated exercises as prescribed by an attending therapist.

Alternatively, the exerciser may be in the form of a fluid-filled body having a football-like shape or other configuration which facilitates grasping thereof by the hands of a user, with a transducer so suspended within the body as to effectively float therein whereby a force applied to the ends of the body acts pneumatically or hydraulically on the transducer and gives rise to an output which is translated into an audible signal that may be registered or scored in the manner previously described.

I claim:
1. An isometric exerciser comprising:
   A. a pair of spaced bodies which are engageable by respective extremities of a user and are joined together by a link having associated therewith a force-responsive transducer producing an electrical value depending on the pressure or tension force applied to said bodies by said user; and
   B. means responsive to said electrical value to produce an audible signal whose nature depends on the strength of the applied force to advise the user regarding his performance, said bodies and transducer and said audible signal means being combined into a unitary exerciser which is movable by the user in any desired motion pattern in the course of which the signal is heard.

2. An exerciser as set forth in claim 1, wherein the components thereof are ensheathed in a flexible cover to define a unitary structure having a generally oblong configuration.

3. An exerciser as set forth in claim 2, wherein said structure has a length less than 12 inches.

4. An exerciser as set forth in claim 2, wherein said cover is replaceable and has a yieldable surface texture.

5. An exerciser as set forth in claim 1, wherein said means responsive to said value is constituted by a pulse-generating system responsive to said electrical value to produce audible beeps having a tone in the sonic range and having a repetition rate that varies in accordance with said value and therefore as a function of the strength of the applied force.

6. An exerciser as set forth in claim 5, wherein the tone of said beeps increases as a step function of the magnitude of said electrical value.

7. An exerciser as set forth in claim 5, wherein the repetition rate of the beeps within each step varies from a minimum value to a maximum value.

8. An exerciser as set forth in claim 5, wherein the amplitude of beeps increases in accordance with the magnitude of said electrical value.

9. An exerciser as set forth in claim 5, wherein said system includes a free-running multi-vibrator responsive to the output of said transducer, said pulses being applied to an oscillator.

10. An exerciser as set forth in claim 5, further including scoring means responsive to the beeps produced in a predetermined period.

11. An exerciser as set forth in claim 10, wherein said scoring means counts the number of cycles of the tones.

12. An exerciser as set forth in claim 10, wherein said scoring means includes an adjustable timer to determine said predetermined period.

13. An exerciser as set forth in claim 12, wherein said timer produces signals indicative of the beginning and end of said period.

14. An exerciser as set forth in claim 13, wherein said timer is programmed to provide a series of periods with dead spaces therebetween.

* * * * *